(12) United States Patent
Gravitt

(10) Patent No.: US 11,952,210 B2
(45) Date of Patent: Apr. 9, 2024

(54) ATTACHED LID CONTAINER WITH RFID TAG

(71) Applicant: Rehrig Pacific Company, Los Angeles, CA (US)

(72) Inventor: Derek Gravitt, Buford, GA (US)

(73) Assignee: Rehrig Pacific Company, Los Angeles, CA (US)

( * ) Notice: Subject to any disclaimer, the term of this patent is extended or adjusted under 35 U.S.C. 154(b) by 0 days.

(21) Appl. No.: 17/716,003

(22) Filed: Apr. 8, 2022

(65) Prior Publication Data

US 2022/0324640 A1   Oct. 13, 2022

Related U.S. Application Data

(60) Provisional application No. 63/172,208, filed on Apr. 8, 2021.

(51) Int. Cl.
| | |
|---|---|
| *B65F 1/14* | (2006.01) |
| *A61B 50/36* | (2016.01) |
| *G06K 19/07* | (2006.01) |
| *G06K 19/077* | (2006.01) |

(52) U.S. Cl.
CPC ............ *B65F 1/1484* (2013.01); *A61B 50/36* (2016.02); *G06K 19/0723* (2013.01); *G06K 19/07758* (2013.01); *B65F 2210/138* (2013.01)

(58) Field of Classification Search
CPC .............................. A61B 50/36; G06K 19/0723

USPC .......................................................... 235/375
See application file for complete search history.

(56) References Cited

U.S. PATENT DOCUMENTS

| | | | | |
|---|---|---|---|---|
| 2008/0094224 A1* | 4/2008 | Parker | ................... | B65F 1/1646 340/572.8 |
| 2010/0276839 A1* | 11/2010 | Parker | ................. | B29C 45/4407 264/238 |
| 2015/0166244 A1* | 6/2015 | Wood | ...................... | B31B 50/74 220/592.25 |
| 2021/0150159 A1* | 5/2021 | Volkerink | .......... | G06K 7/10366 |
| 2022/0079141 A1* | 3/2022 | Mi | ........................ | A01N 1/0257 |
| 2022/0081209 A1* | 3/2022 | Cristescu | ............. | B65G 1/0464 |
| 2022/0258915 A1* | 8/2022 | Srichai | ................. | B65D 77/061 |

OTHER PUBLICATIONS ip.com.*

* cited by examiner

*Primary Examiner* — Allyson N Trail
(74) *Attorney, Agent, or Firm* — Carlson, Gaskey & Olds, P.C.

(57) ABSTRACT

A container includes a base. A plurality of walls extends upward from the base. At least one handle is located on one of the plurality of walls. A slot is in one of the base, the plurality of walls or the at least one handle. The slot is at least partially defined by a pair of opposing walls with at least one retention projection extending from each of the pair of opposing walls.

37 Claims, 21 Drawing Sheets

ATTACHED LID CONTAINER WITH RFID TAG

CROSS-REFERENCE TO RELATED APPLICATIONS

This application claims priority to U.S. Provisional Application No. 63/172,208, filed Apr. 8, 2021.

BACKGROUND OF THE INVENTION

The present disclosure relates generally to containers and more particularly to an attached lid container associated with an RFID tag.

In hospital surgical rooms, medical waste containers are often attached lid containers. The containers include a base wall, a pair of opposed side walls, and a pair of opposed end walls extending up from the periphery of the base wall. Lids are attached to the upper edge of the side walls by hinges, and the opposite ends of the lids interlock with one another to selectively close the container. During use, a plastic bag is placed in the container with the upper edge of the bag folded back outwardly over the upper periphery of the open container.

SUMMARY

In one exemplary embodiment, a container includes a base. A plurality of walls extends upward from the base. At least one handle is located on one of the plurality of walls. A slot is in one of the base, the plurality of walls or the at least one handle. The slot is at least partially defined by a pair of opposing walls with at least one retention projection extending from each of the pair of opposing walls.

In another exemplary embodiment, a method of securing an RFID tag relative to a container includes moving an RFID tag along at least one retention projection located in a slot on the container. An edge of the RFID tag is engaged with a portion of the at least one retention.

These and other features of the disclosed examples can be understood from the following description and the accompanying drawings, which can be briefly described as follows.

DETAILED DESCRIPTION OF THE PREFERRED EMBODIMENT

Figure 1:
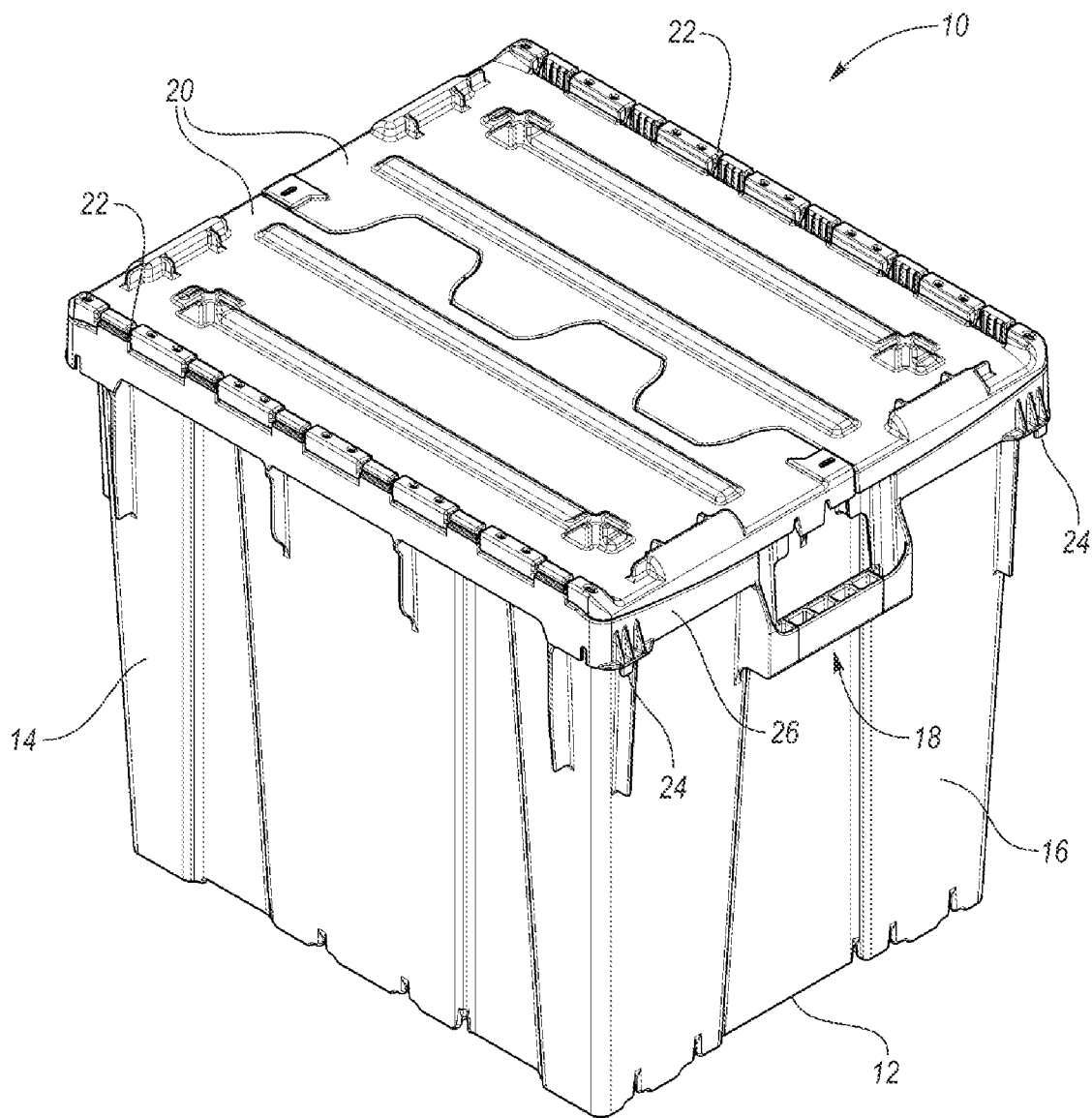
FIG. 1 is a perspective view of a container according to one example of the present disclosure.

FIG. 1 is a perspective view of a container 10 according to one example embodiment of the present disclosure. The container 10 includes a base wall 12, opposed side walls 14 (or long walls) and opposed end walls 16 (or short walls) extending upward from the periphery of the base wall 12. A handle assembly 18 is located in the end walls 16. Lids 20 are hingeably connected to upper edges of the side walls 14 by hinges 22. The lids 20 have interleaving portions at their outer ends, as is known for attached-lid containers.

The container 10 is provided with a plurality of hooks 24 (for example, two hooks 24) projecting from the upper lip 26. The hooks 24 in the illustrated example are disposed at outer edges of the end walls 16, adjacent the hinges 22. The position of the hooks 24 is important, but could vary based upon the design of the container 10, including the lids 20 and hinges 22.

Figure 2:
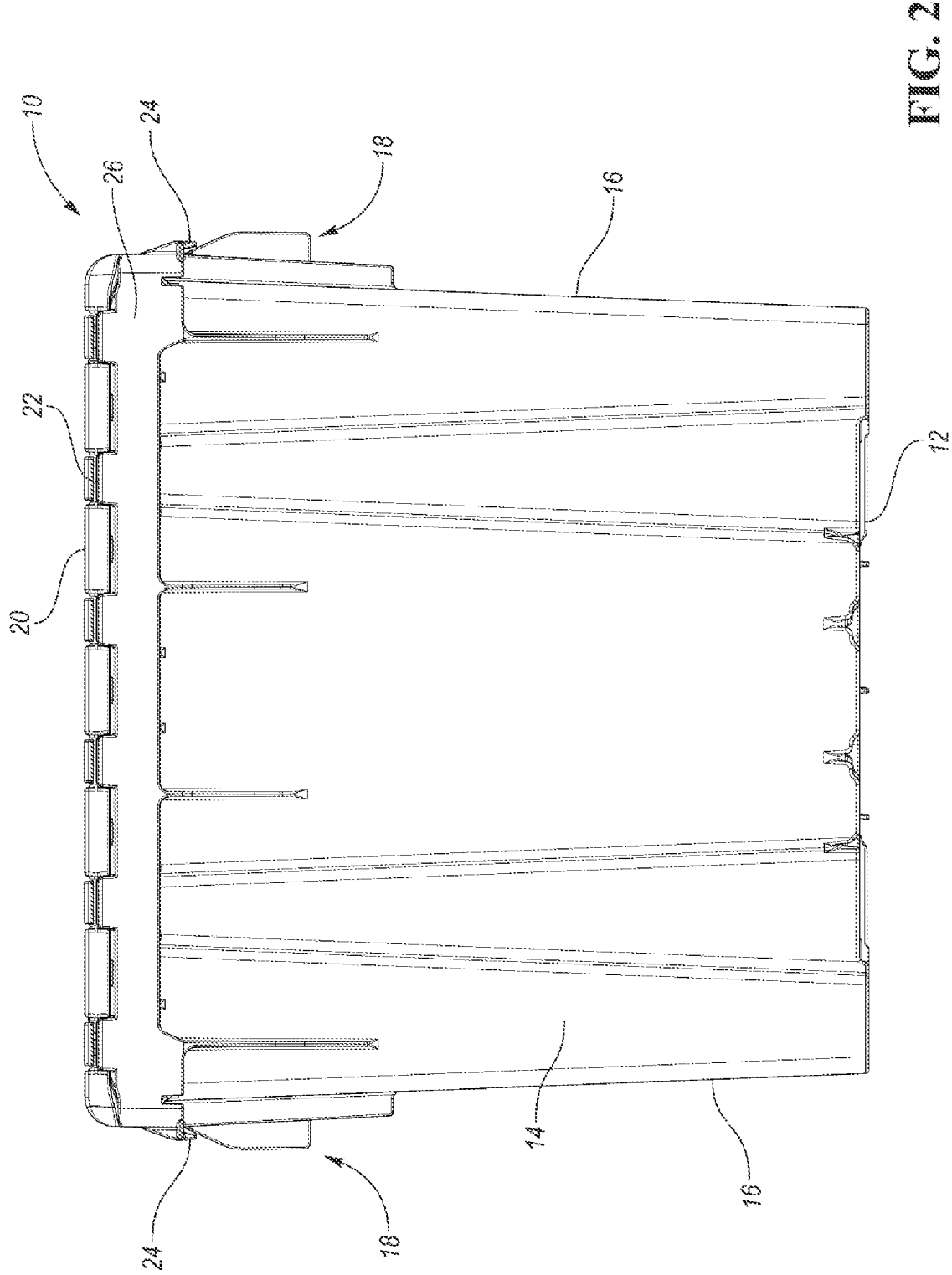
FIG. 2 is a side view of the container of FIG. 1.

As shown in FIG. 2, the hooks 24 project outwardly and downwardly from the lip 26. The hooks 24 are aligned with inner edges of hinges 22 connecting the lids 20 to the side walls 14. The hooks 24 are aligned with the side walls 14.

Figure 3:
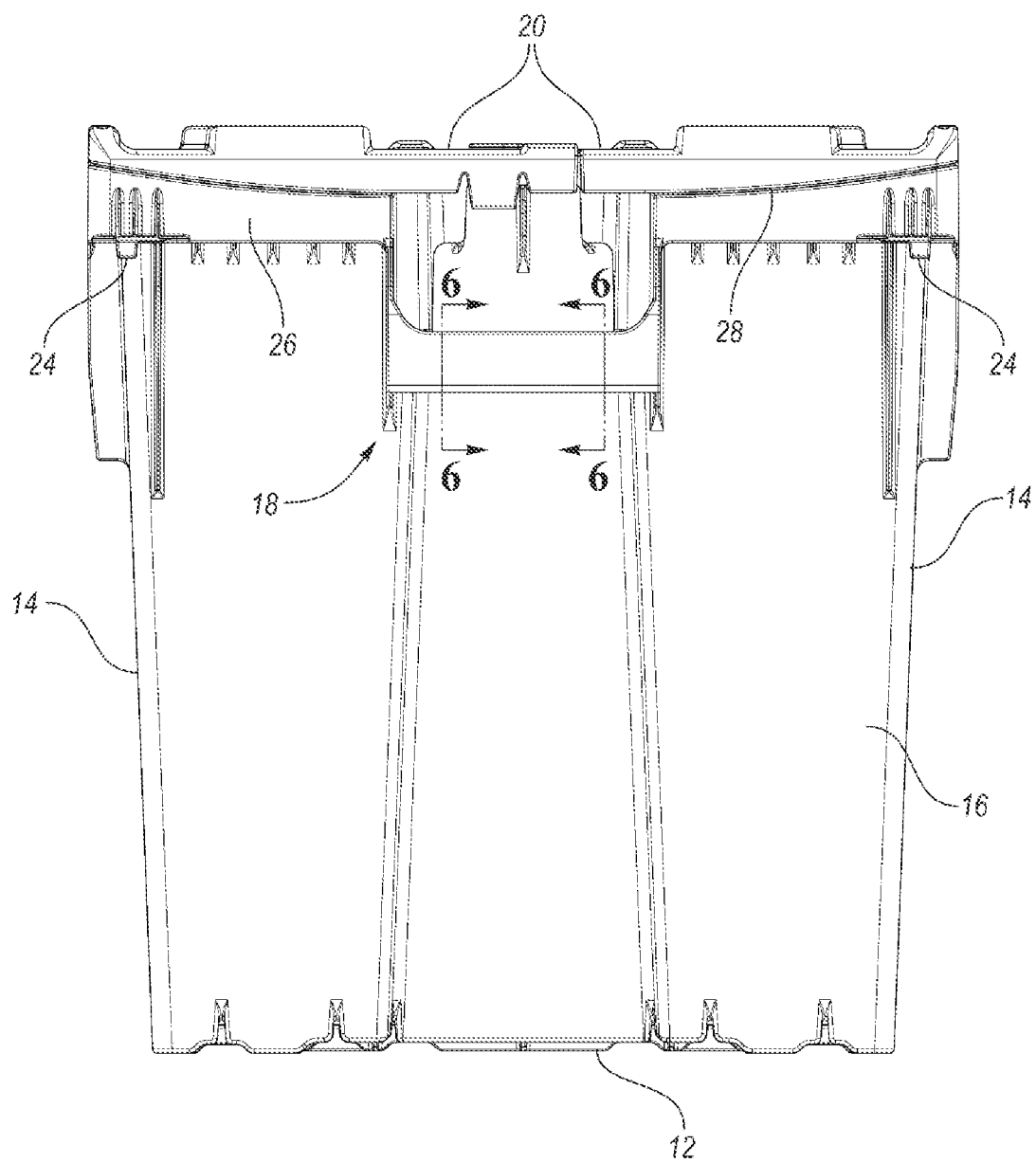
FIG. 3 is an end view of the container of FIG. 1.

FIG. 3 is an end view of the container 10. As shown in FIG. 3, the lids 20 each include angled ribs 28 on end edges of the lids 20. The angled ribs 28 taper toward the hinges 22.

Figure 4:
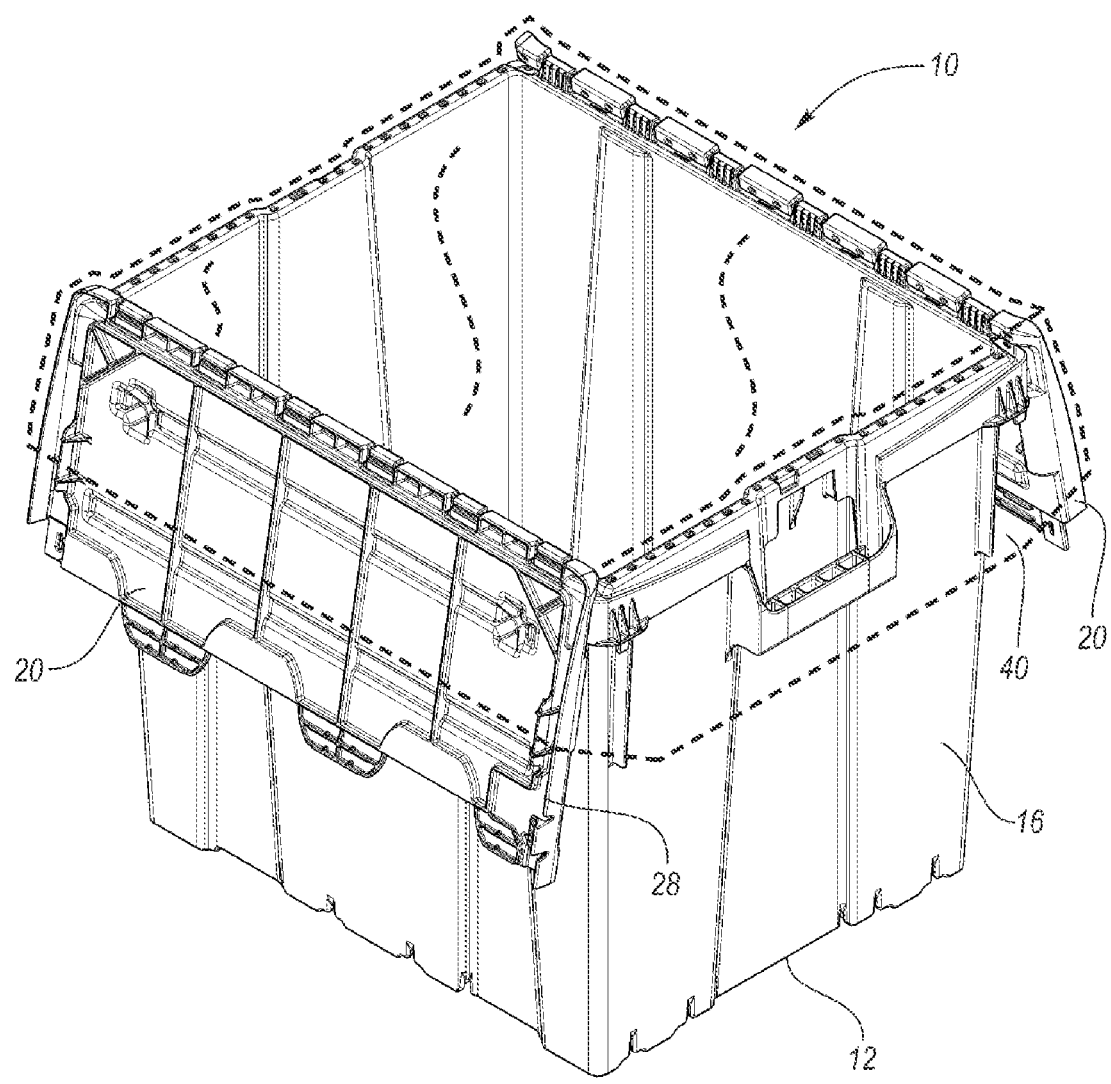
FIG. 4 illustrates the container of FIG. 1 with the lids opened and a plastic bag inserted therein.

In FIG. 4, the container 10 is shown with a plastic bag 40 placed therein. The plastic bag 40 is placed in the container 10, such that the bottom of the bag 40 rests on the base wall 12, while the side walls of the bag 40 are generally aligned with the walls 14, 16 of the container 10. The upper edge of the bag 40 is folded over the upper edges of the container 10, and is folded over the lids 20, which are adjacent the side walls 14 and hanging substantially downwardly in the open position. The bag 40 extends over the edges of the end walls 16 and over the hooks 24.

Without any other action required by the user, by simply pivoting the lids 20 from the open position toward the closed position, the bag 40 slides up the angled ribs 28 on end edges of the lids 20 and portions of the bag 40 are caught under the hooks 24 on both end walls 16. As the lids 20 are pivoted all the way to the closed position, the bag 40 is retained under the hooks 24 and pulled tight across the hooks 24.

Figure 5:
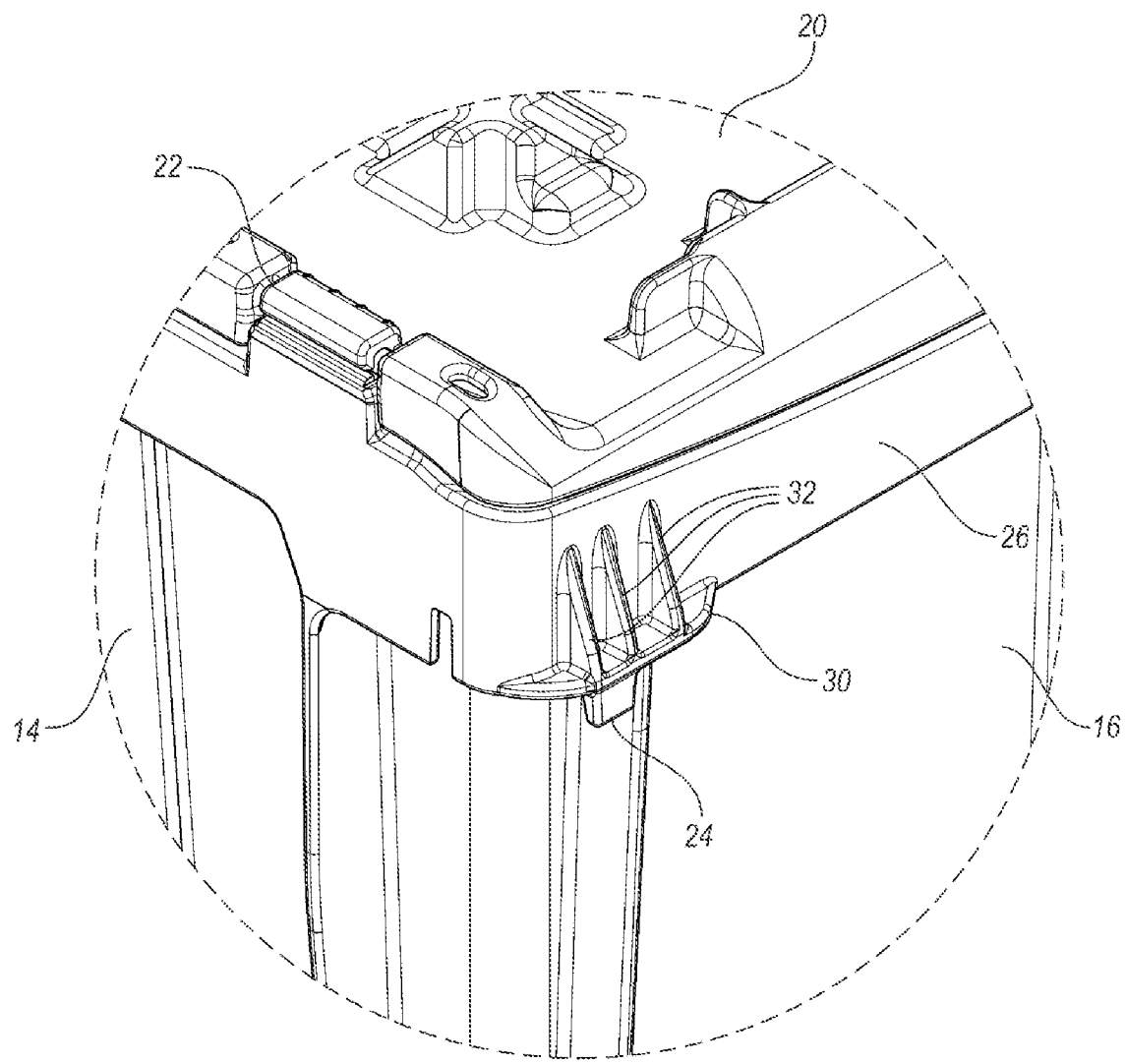
FIG. 5 illustrates an enlarged view of a corner of the container of FIG. 1.

As shown in FIG. 5, the hook 24 is located on a ledge 30 that protrudes from the upper lip 26. The hook 24 is located on a side of the ledge 30 facing the base wall 12. Multiple ribs 32, such as three ribs, are located on an opposite side of the ledge 30 from the hook 24 and engage the upper lip 26. Additionally, the ledge 30 includes a central region having a generally constant spacing from the lip 26 that tapers to the lip 26 outward of the ribs 32. One feature of the configuration of the ribs 32 and the ledge 30 is a greater load transfer area to the lip 26 to prevent the hook 24 from deforming relative to the lip 26.

Figure 6:
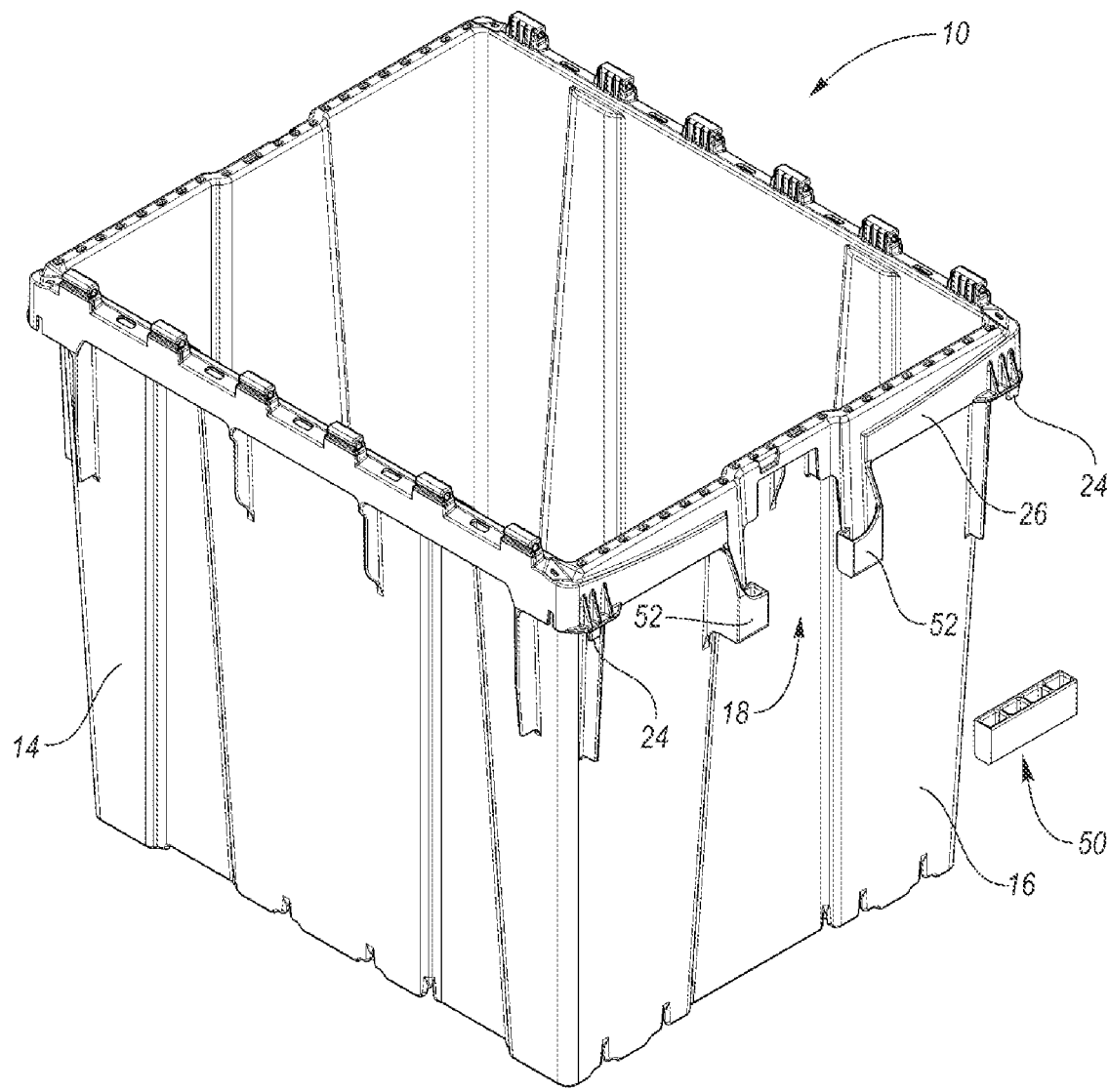
FIG. 6 illustrates a handle section removed from the container along the lines 6-6 of FIG. 3.

FIG. 6 illustrates a handle section 50 of the handle assembly 18 positioned relative to the end wall 16. The handle section 50 is shown cut along lines 6-6 of FIG. 3 for illustrative purposes. The handle section 50 is integral with remainder of the container 10 through projections 52 and is formed during an injection molding process in a mold. However, the mold for the container 10 can be configured to allow for the use of different mold inserts that correspond to one of the handle sections 50A-50D described below.

Figure 7:
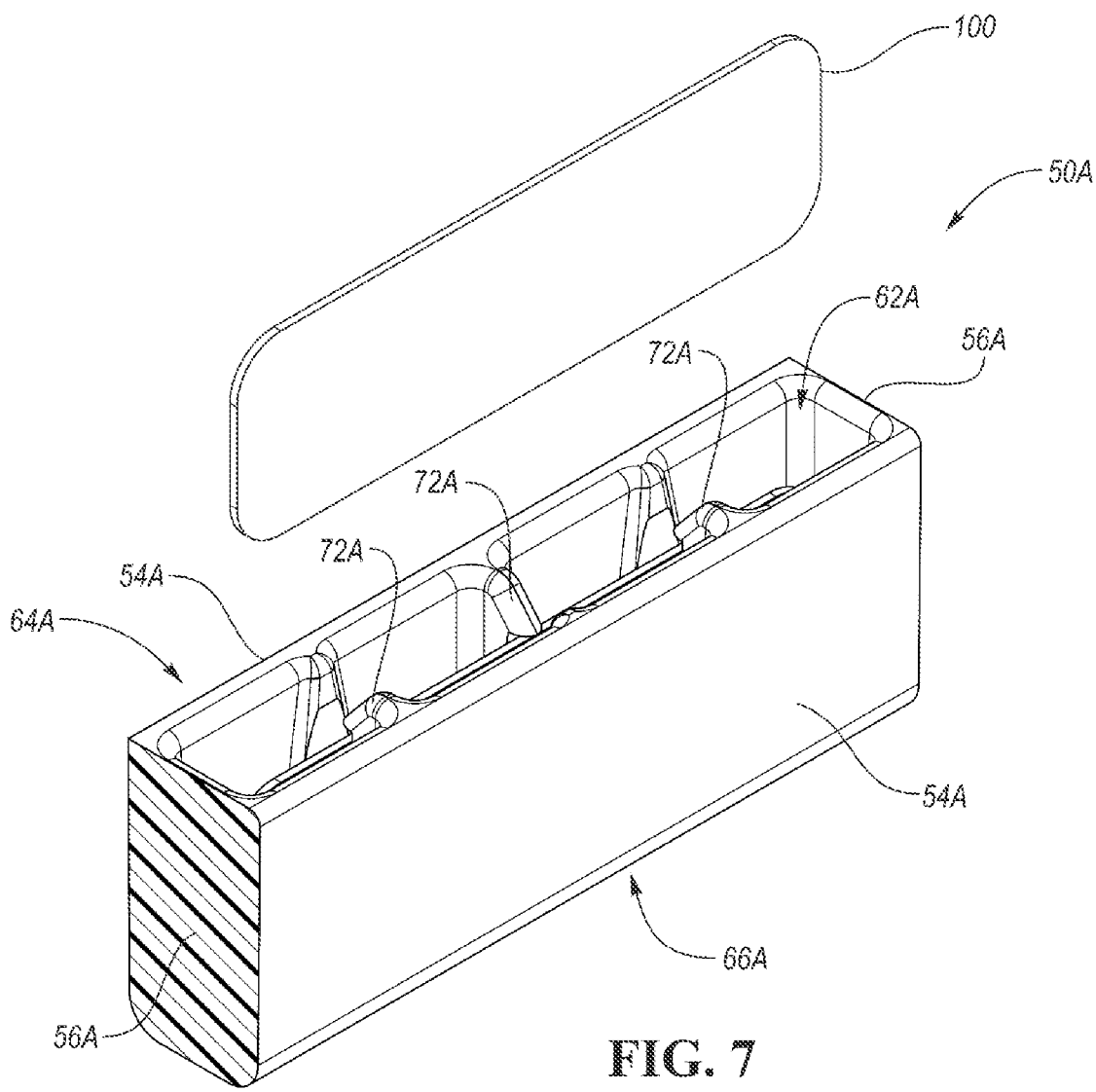
FIG. 7 illustrates an RFID tag positioned relative to an example handle section.
Figure 8:
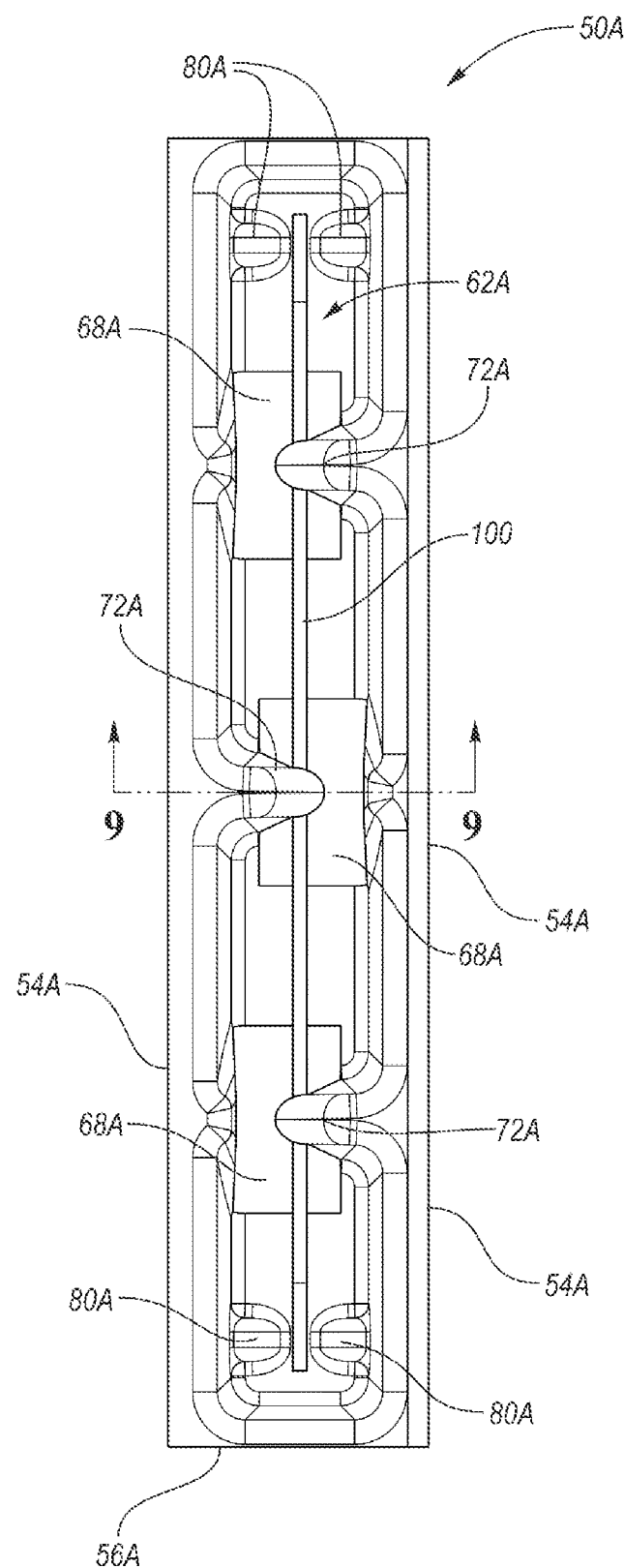
FIG. 8 illustrates a top view of the handle section of FIG. 7 with the RFID tag inserted into the handle section.
Figure 9:
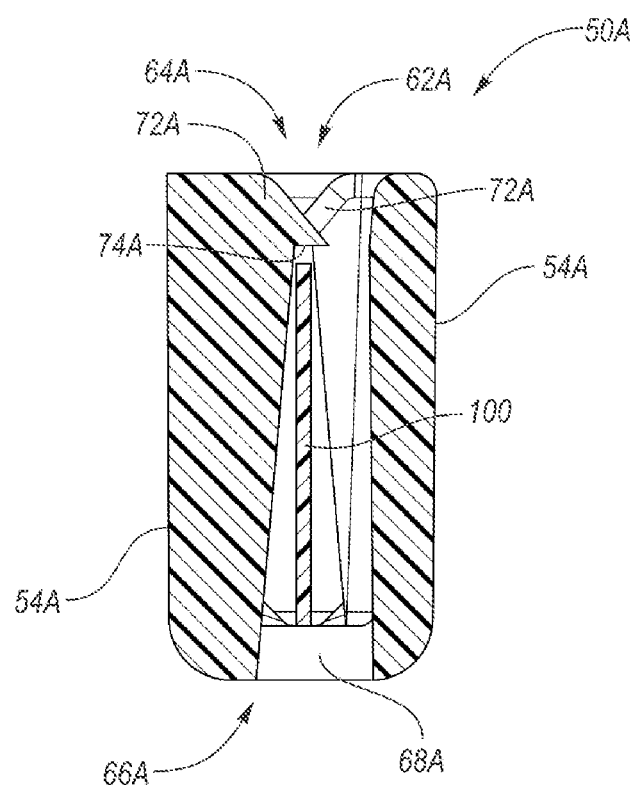
FIG. 9 illustrates a cross-sectional view of the handle section of FIG. 8 along line 9-9.
Figure 10:
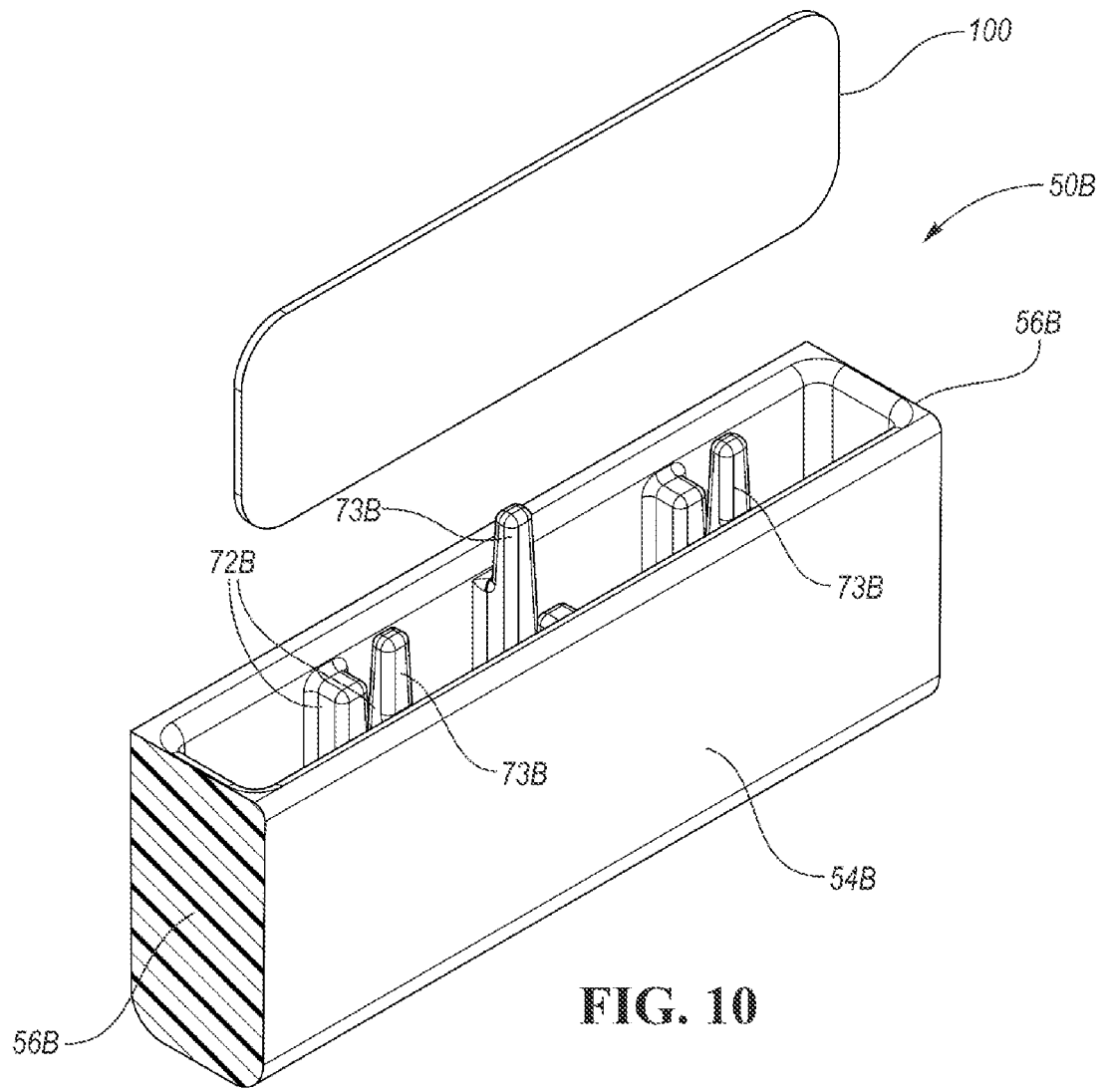
FIG. 10 illustrates the RFID tag positioned relative to another example handle section.

FIGS. 7-9 illustrate an example handle section 50A for use in the handle assembly 18 described above. The handle section 50A is elongated and includes a rectangular cross section defined by opposing side walls 54A and opposing end walls 56A that surround an inner passage 62A or slot. The inner passage 62A extends from a top side 64A to a bottom side 66A of handle section 50A to allow for drainage of liquids though the handle section 50A. At least one wall segment 68A extends between the side walls 54A adjacent the bottom side 66A and includes an upper surface for contacting an RFID tag 100 as shown in FIG. 9. The RFID tag 100 includes an antenna for communicating with a receiver (not shown) information about the container 10, such as ownership or products stored therein.

The inner passage 62A includes multiple opposing retention projections 72A that extend from opposing sides of the inner passage 62A. The retention projections 72A are longitudinally spaced from each other and include a ledge 74A facing the wall segment 68A as shown in FIG. 9. The ledge 74A is located closer to the top side 64A than the bottom side 66A and a distance from the ledge 74A to the wall segment 68A is equal to or greater than a height of the RFID tag 100. A depth of the ledge 74A is also equal to or greater than a thickness of the RFID tag 100. The ledge 74A intersects a first tapered wall 76A at an outer edge and a second tapered wall 78A at an inner edge.

In addition to the retention projections 72A, the inner passage 62A also includes pairs of centering tabs 80A for centering the RFID tag 100 in the inner passage 62A adjacent each end wall 56A. In the illustrated example, the pairs of centering tabs 80A are located closer to the bottom side 66A than the top side 64A. One feature of using the centering tabs 80A in connection with the retention projections 72A is the ability for the RFID tag 100 to snap into the handle section 50A to secure the RFID tag 100 relative to the container 10. This configuration also allows for the RFID tag 100 to be removed from the handle section 50A by deforming the RFID tag 100 around the retention projections 72A.

FIGS. 10-13 illustrate another example handle section 50B. The handle section 50B is similar to the handle section 50A except where described below or shown in the Figures. Similar elements will be identified with an ending "B" in place of an ending "A."

The handle section 50B is defined by opposing side walls 54B and opposing end walls 56B that surround an inner passage 62B. The inner passage 62B extends from a top side 64B to a bottom side 66B of handle section 50B to allow for drainage of liquids though the handle section 50B. At least one wall segment 68B extends between the side walls 54B adjacent the bottom side 66B and includes an upper surface for contacting the RFID tag 100.

Figure 11:
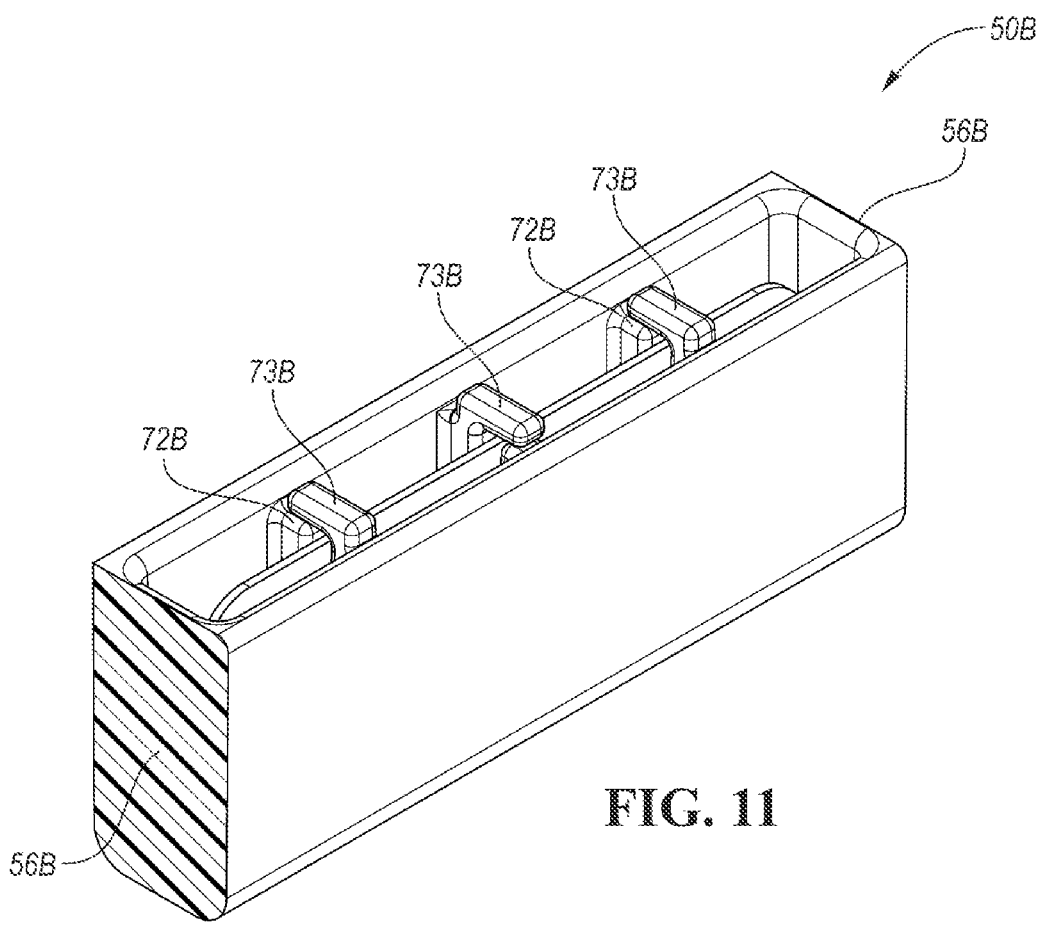
FIG. 11 illustrates a perspective view of the RFID tag inserted into the handle section of FIG. 10.
Figure 12:
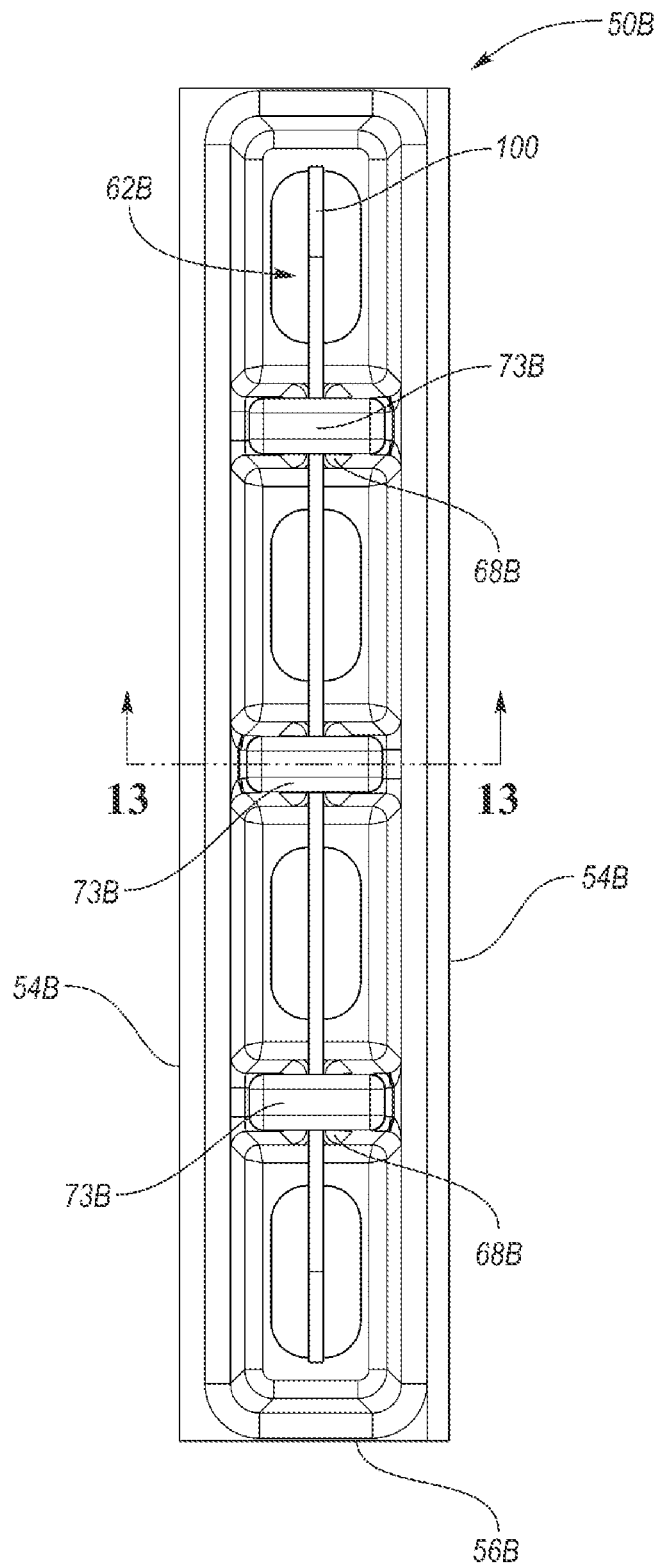
FIG. 12 illustrates a top view of the RFID tag inserted into the handle section of FIG. 10.

Pairs of opposing projections 72B are aligned with each other across the inner passage 62B or slot. One of the projections 72B in each pair of aligned projections 72B includes a deformable post 73B extending upward and out of the inner passage 62B of the handle section 50B. In the illustrated example, the posts 73B are located on projections 72B on alternating sides of the inner passage 62B such that they fold over in an alternating pattern as shown in FIG. 11.

Figure 13:
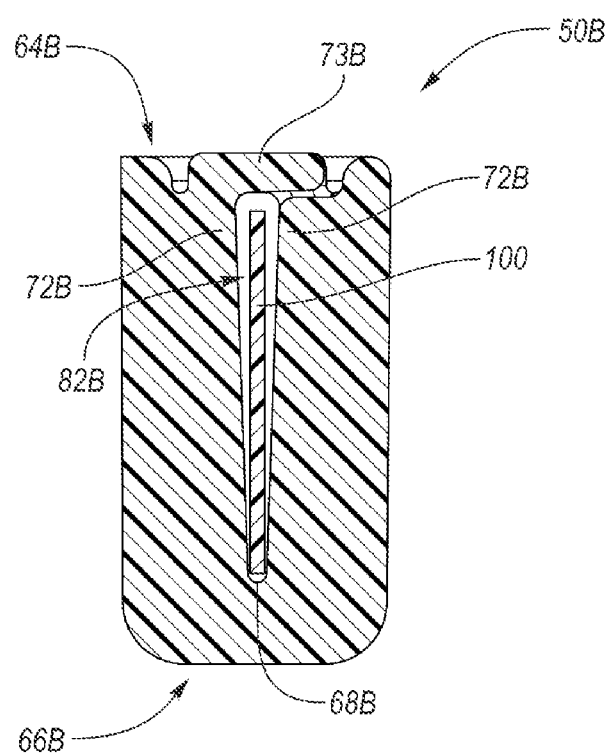
FIG. 13 illustrates a cross-sectional view taken along line 13-13 of FIG. 12.
Figure 14:
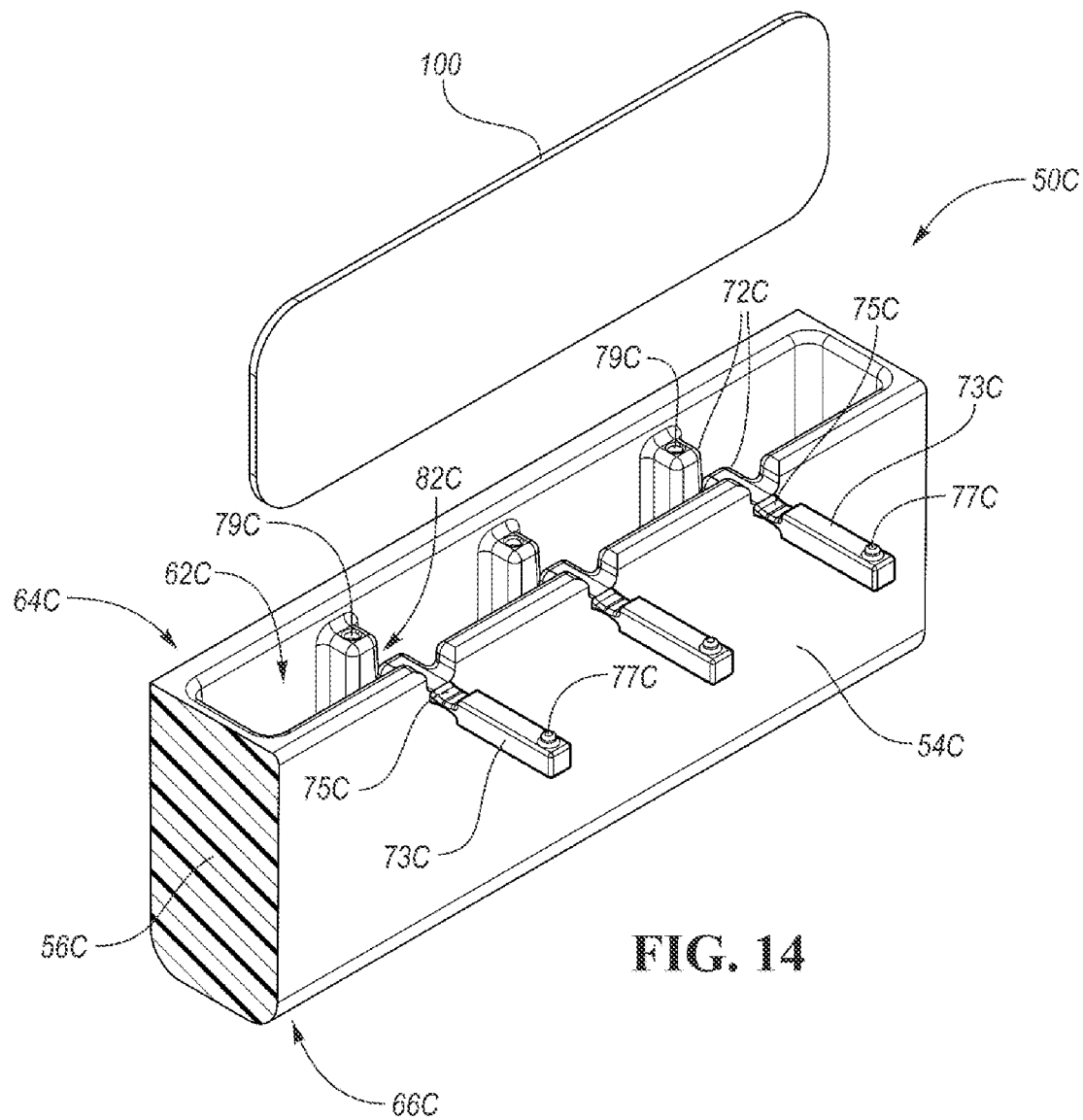
FIG. 14 illustrates the RFID tag positioned relative to yet another example handle section.
Figure 15:
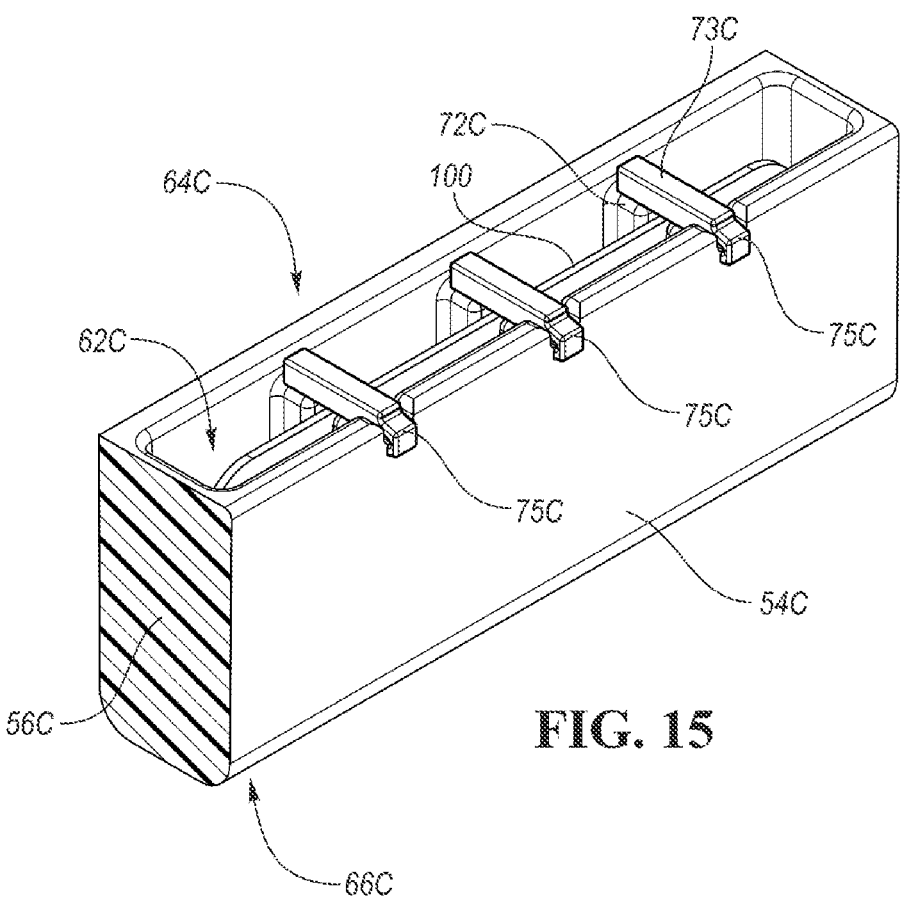
FIG. 15 illustrates a perspective view of the RFID tag inserted into the handle section of FIG. 14.
Figure 16:
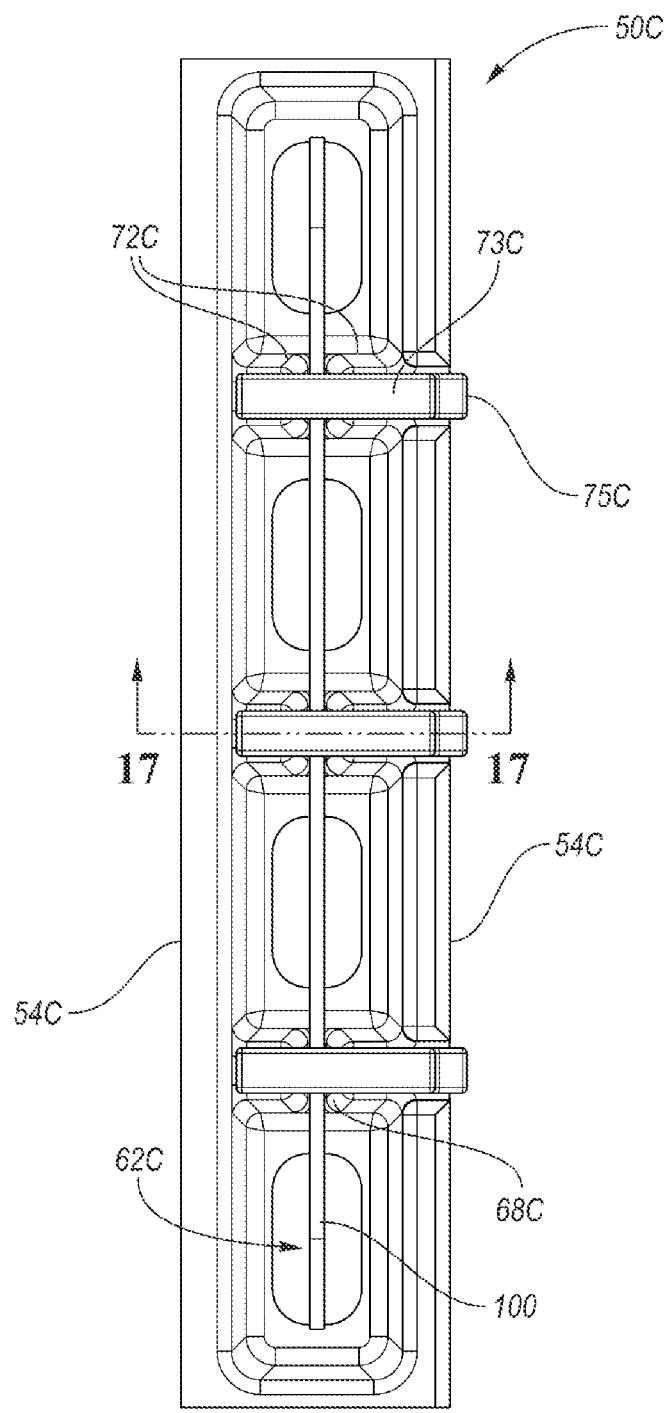
FIG. 16 illustrates a top view of the RFID tag inserted into the handle section of FIG. 14.
Figure 17:
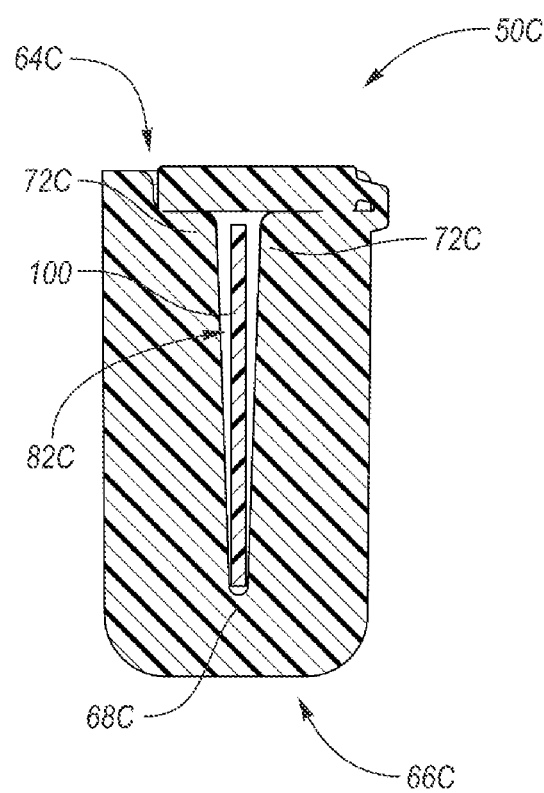
FIG. 17 illustrates a cross-sectional view taken along line 17-17 of FIG. 16.

As shown in FIG. 13, the pairs of projections 72B create a spacing 82B for accepting the RFID tag 100 that tapers from the top side 64B to the bottom side 66B. The deformable post 73B extends parallel to a corresponding one of the projections 72B in a first position and perpendicular to the corresponding one of the projections 72B in a second position. Once the deformable posts 73B are bent over the spacing 82B to the second position, the RFID tag 100 is secured relative to the handle section 50B. The posts 73B can be deformed until they contact the adjacent projection 72B across the spacing 82B or the posts 73B can also be attached to the adjacent projection 72B through an ultrasonic welding process, a hot plate welding process, or another similar process to further prevent the post 73B from separating from the adjacent projection 72B.

FIGS. 14-17 illustrate another example handle section 50C. The handle section 50C is similar to the handle sections 50A-B except where described below or shown in the Figures. Similar elements will be identified with an ending "C."

The handle section 50C is defined by opposing side walls 54C and opposing end walls 56C that surround an inner passage 62C or slot. The inner passage 62C extends from a top side 64C to a bottom side 66C of handle section 50C. At least one wall segment 68C extends between the opposing side walls 54C adjacent the bottom side 66C and includes an upper surface for contacting the RFID tag 100.

Pairs of opposing projections 72C are aligned with each other across the inner passage 62C. Tabs 73C are attached to one of the side walls 54C or projections 72C by a living hinge 75C to allow the tabs 73C bend over a spacing 82C between the projections 72C. Distal ends of the tabs 73C include a first snap feature 77C that mate with a second snap feature 79C on an opposing projection 72C to lock the RFID tag 100 relative to the handle section 50C. The first and second snap features 77C and 79C also allow the RFID tag 100 to be removed from the handle section 50C without damaging the tabs 73C.

FIGS. 18-21 illustrate another example handle section 50D. The handle section 50D is similar to the handle sections 50A-C except where described below or shown in the Figures. Similar elements will be identified with an ending "D."

The handle section 50D is defined by opposing side walls 54D and opposing end walls 56D that surround an inner passage 62D. The inner passage 62D extends from a top side 64D to a bottom side 66D of handle section 50D. Wall segments 68D extends between the side walls 54D adjacent the bottom side 66D and includes an upper surface for contacting the RFID tag 100.

Figure 18:
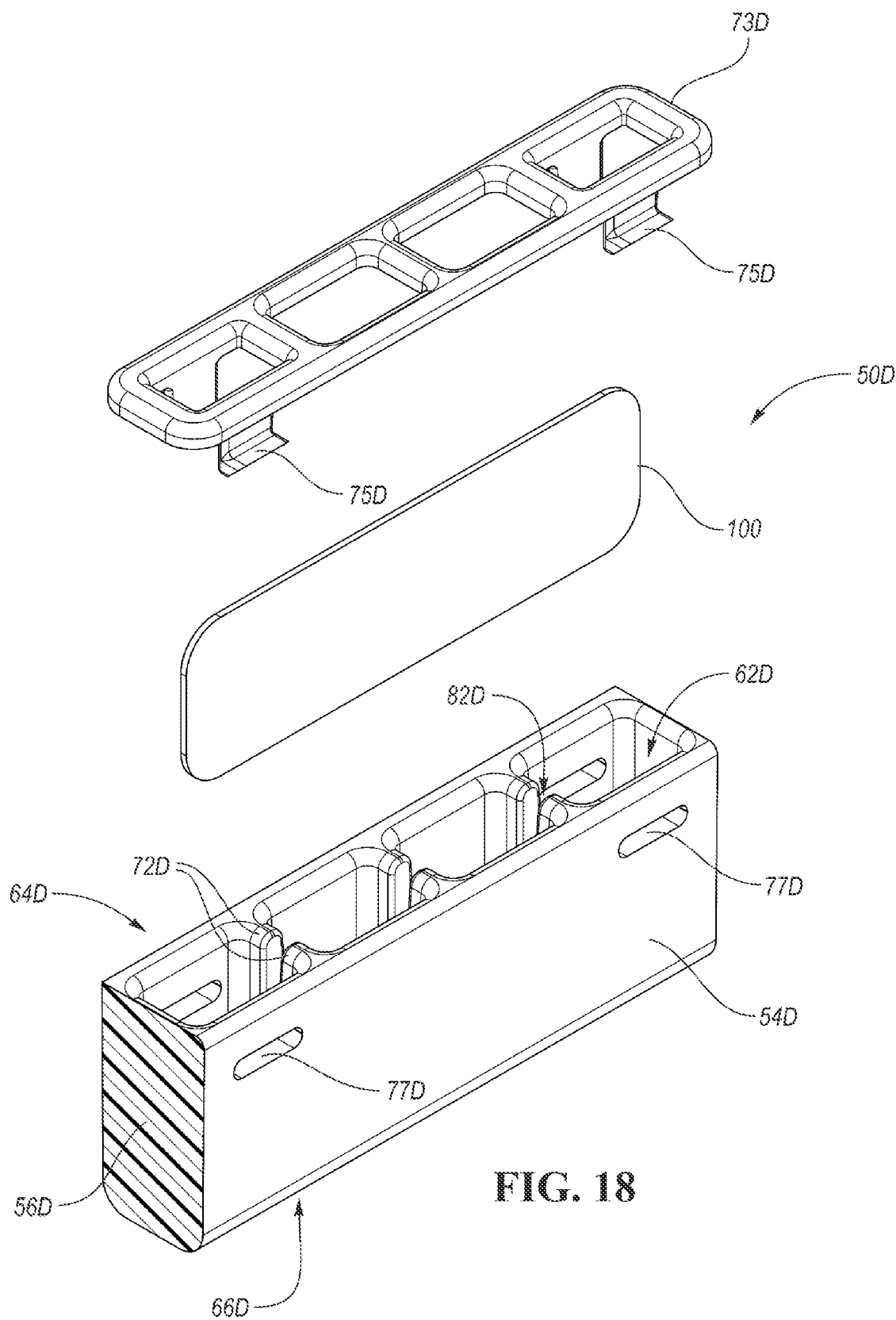
FIG. 18 illustrates the RFID tag positioned relative to a further example handle section.
Figure 19:
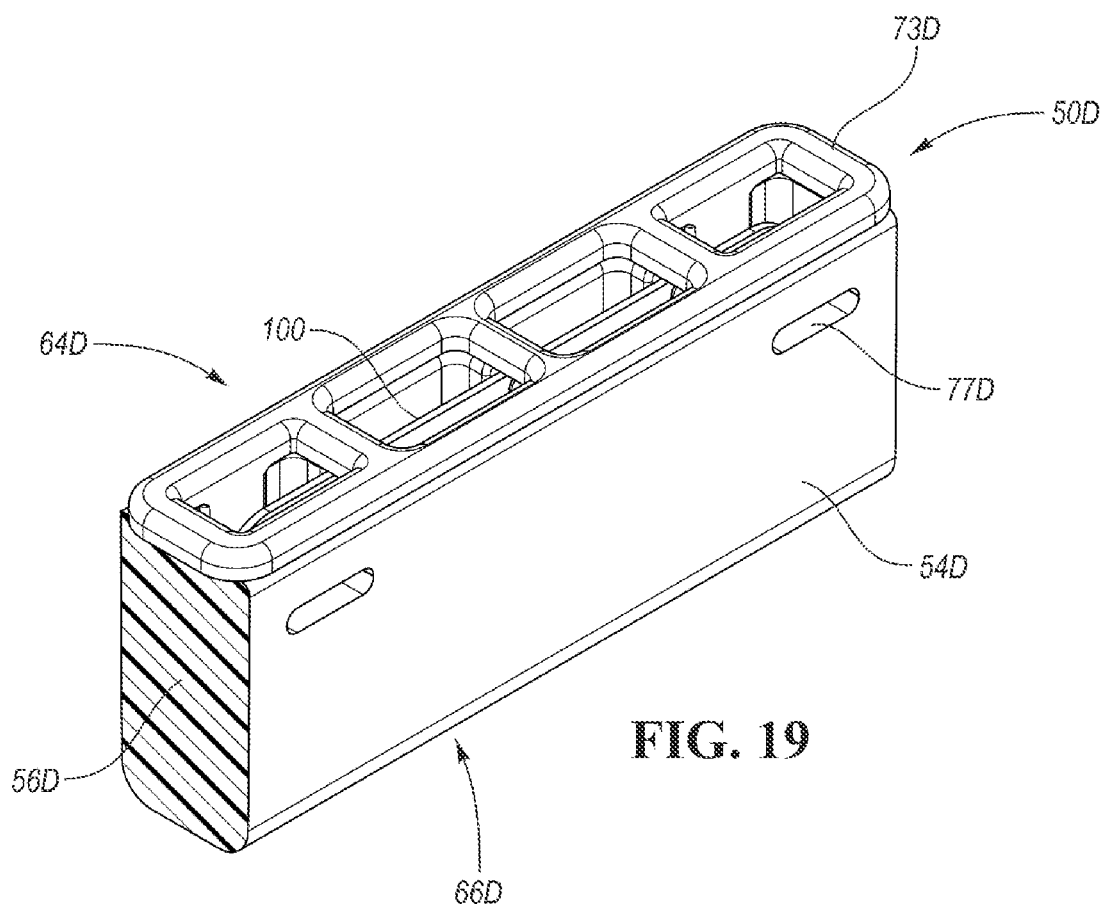
FIG. 19 illustrates a perspective view of the RFID tag inserted into the handle section of FIG. 18.
Figure 20:
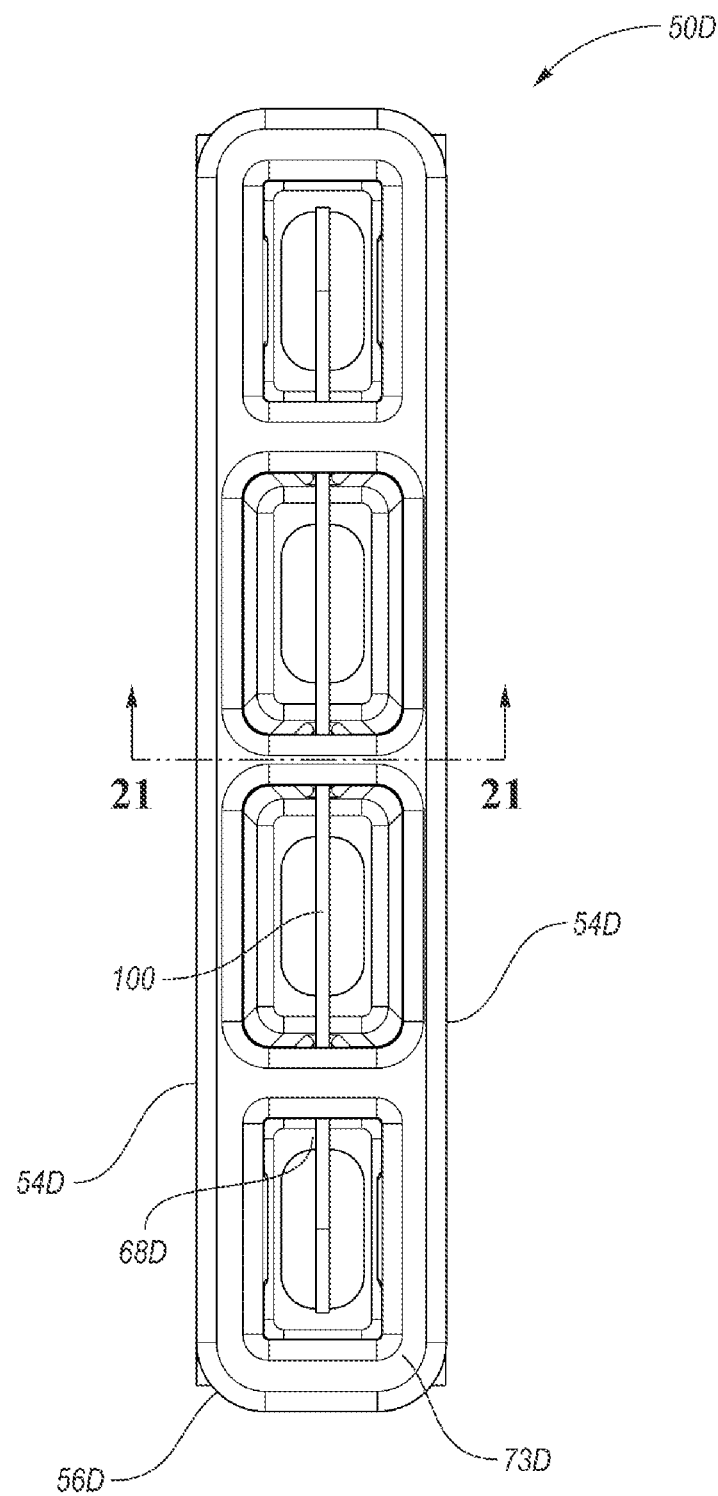
FIG. 20 illustrates a top view of the RFID tag inserted into the handle section of FIG. 18.
Figure 21:
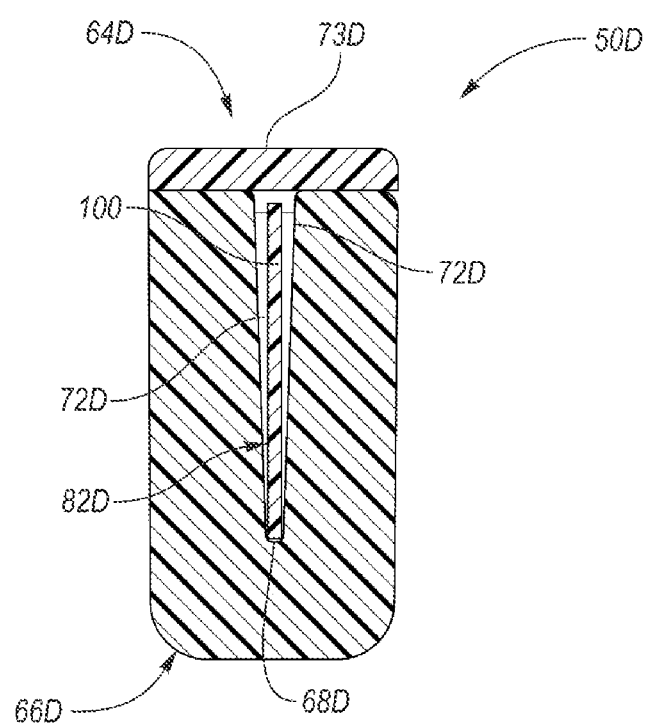
FIG. 21 illustrates a cross-sectional view taken along line 21-21 of FIG. 18.

Pairs of opposing projections 72D are aligned with each other across the inner passage 62D to define a spacing 82D for accepting the RFID tag 100 as shown in FIGS. 18 and 21. A cover 73D encloses the spacing 82D to retain the RFID tag 100 relative to the container 10. The cover 73D includes a perimeter rail defining a plurality of openings with connecting members extending between the perimeter rail. Opposing pairs of retention tabs 75D extend from the perimeter rail for engaging retention openings 77D in the opposing side walls 54D.

Although the different non-limiting examples are illustrated as having specific components, the examples of this disclosure are not limited to those particular combinations. It is possible to use some of the components or features from any of the non-limiting examples in combination with features or components from any of the other non-limiting examples.

It should be understood that like reference numerals identify corresponding or similar elements throughout the several drawings. It should also be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claim should be studied to determine the true scope and content of this disclosure.

What is claimed is:

1. A container comprising:
    a base;
    a plurality of walls extending upward from the base;
    at least one handle located on one of the plurality of walls; and
    a slot in one of the base, the plurality of walls, or the at least one handle, the slot at least partially defined by a pair of opposing walls with at least one retention projection extending from each of the pair of opposing walls, and wherein the at least one retention projection extends outwardly of each of the opposing walls in a direction that is non-parallel to an insertion direction of the slot.

2. The container of claim 1, including an RFID tag located in the slot, and wherein the at least one retention projection extends outwardly of each of the opposing walls in a direction that is perpendicular to a planar face of the RFID tag.

3. The container of claim 1, wherein the slot is located in the at least one handle and the slot forms an inner passage through the at least one handle.

4. The container of claim 3, wherein the at least one handle is spaced outward from one of the plurality of walls and the slot forms an inner passage through the at least one handle that is free from hinges.

5. The container of claim 1, wherein the at least one retention projection includes an RFID tag contact surface that faces a base of the slot.

6. The container of claim 5, wherein the at least one retention projection includes a first retention projection on a first one of the pair of opposing walls and at least two retention projections on a second one of the pair of opposing walls.

7. The container of claim 6, wherein the at least two retention projections are offset from the first retention projection along a length of the slot.

8. The container of claim 1, wherein the retention projection includes a ledge having a contact surface that faces a base of the slot.

9. The container of claim 1, wherein the at least one retention projection includes at least one pair of retention projections that extend from opposing walls of the slot and are longitudinally aligned with each other in the slot.

10. The container of claim 9, including a tab pivotably attached to the container and configured to move between a first position spaced from the at least one pair of retention projections to a second position engaging one of the pair of retention protections.

11. The container of claim 1, wherein the at least one retention projection includes a contact surface that contacts an RFID tag surface.

12. A container comprising:
    a base;
    a plurality of walls extending upward from the base;
    at least one handle located on one of the plurality of walls;
    a slot in one of the base, the plurality of walls, or the at least one handle, the slot at least partially defined by a pair of opposing walls with at least one retention projection extending from each of the pair of opposing walls;
    wherein the at least one retention projection includes an RFID tag contact surface that faces a base of the slot; and
    a first pair of centering tabs located adjacent a first end of the slot and a second pair of centering tabs located adjacent a second opposite end of the slot.

13. The container of claim 12, wherein the at least one retention projection is located inward from both the first and second pairs of centering tabs in the slot.

14. The container of claim 13, wherein the at least one retention projection extends more than 50% of a width of the slot.

15. The container of claim 12, wherein the retention projection is located entirely in the slot.

16. A container comprising:
    a base;
    a plurality of walls extending upward from the base;
    at least one handle located on one of the plurality of walls;
    a slot in one of the base, the plurality of walls, or the at least one handle, the slot at least partially defined by a pair of opposing walls with at least one retention projection extending from each of the pair of opposing walls;
    wherein the at least one retention projection includes at least one pair of retention projections that extend from opposing walls of the slot and are longitudinally aligned with each other in the slot; and
    wherein one retention projection of the at least one pair of retention projections includes a post located at a distal end of the retention projection that extends outward of the slot in a first position and is located in the slot in a second position.

17. The container of claim 16, wherein a length of the post is greater than a distance between the pair of retention projections.

18. The container of claim 16, wherein the post is parallel to a remainder of a corresponding one of the at least one retention projection in a first position and perpendicular to the remainder of the corresponding one of the at least one retention projection in a second position.

19. A method of securing an RFID tag relative to a container comprising:
    moving an RFID tag in an insertion direction along at least one retention projection located in a slot on the container, wherein the at least one retention projection extends outwardly from a wall of the slot in a direction that is non-parallel to a planar surface of the RFID tag; and
    engaging the RFID tag with a portion of the at least one retention projection.

20. The method of claim 19, including removing the RFID tag from the slot by deforming the RFID tag.

21. The method of claim 19, including providing the at least one retention projection with an RFID tag contact surface that faces a base of the slot.

22. The method of claim 19, including forming the slot in a handle of the container.

23. The method of claim 19, including contacting a surface of the RFID tag against a surface of the at least one retention projection during the step of moving the RFID tag along the at least one retention projection.

24. The method of claim 19, including tapering an outwardly facing surface of the at least one retention projection relative to an outer surface of the wall.

25. A method of securing an RFID tag relative to a container comprising:
   moving an RFID tag along at least one retention projection located in a slot on the container;
   guiding a first end of the RFID tag with a first pair of centering tabs in the slot and guiding a second end of the RFID tag with a second pair of centering tabs in the slot; and
   engaging an edge of the RFID tag with a portion of the at least one retention projection.

26. A method of securing an RFID tag relative to a container comprising:
   moving an RFID tag along at least one retention projection located in a slot on the container; and
   engaging an edge of the RFID tag with a portion of the at least one retention projection, wherein the at least one retention projection comprises a plurality of retention projections, and including
   defining the slot by a pair of opposing walls with at least one retention projection of the plurality of retention projections protruding from an outer surface of each wall of the pair of opposing walls, and
   tapering an outwardly facing surface of the at least one retention projection relative to the outer surface of a respective one of the pair of opposing walls.

27. A container comprising:
   a base;
   a plurality of walls extending upward from the base;
   at least one handle located on one of the plurality of walls; and
   a slot in one of the base, the plurality of walls, or the at least one handle, the slot at least partially defined by a pair of opposing walls with at least one retention projection extending from each of the pair of opposing walls, wherein the at least one retention projection protrudes outwardly of an outer surface of a respective one of the pair of opposing walls, and wherein an outwardly facing surface of the at least one retention projection tapers relative to the outer surface of the respective one of the pair of opposing walls.

28. A container comprising:
   a container body including at least a base and a plurality of walls; and
   a slot in the container body, the slot at least partially defined by a pair of opposing walls with at least one retention projection extending outwardly of an outer surface of at least one wall of the pair of opposing walls in a direction that is non-parallel to an insertion direction of the slot.

29. The container of claim 28, wherein the at least one retention projection includes a contact surface that contacts an RFID tag surface.

30. The container of claim 28, wherein the container body includes at least one handle, and wherein the slot is in the at least one handle.

31. The container of claim 28, wherein the at least one retention projection comprises at least a first retention projection and a second retention projection, and wherein the first retention projection protrudes from the outer surface of a first wall of the pair of opposing walls and the second retention projection protrudes from the outer surface of a second wall of the pair of opposing walls, and wherein an RFID tag is captured within the slot at least between the first retention projection and the second retention projection.

32. The container of claim 28, wherein the at least one retention projection comprises one or more pairs of opposing projections that define a spacing that accepts an RFID tag, and wherein:
   each pair of opposing projections are aligned with each other across the spacing, or
   each pair of opposing projections are offset from each other across the spacing.

33. The container of claim 32, including a cover that encloses the spacing to retain the RFID tag relative to the container.

34. The container of claim 28, wherein the at least one retention projection comprises a ledge having a contact surface that faces a base of the slot.

35. The container of claim 28, wherein the at least one retention projection comprises a plurality of retention projections that are spaced apart from each other and extend along a length of the slot.

36. The container of claim 28, wherein the at least one retention projection retains an RFID tag to the container, and wherein the at least one retention projection extends outwardly of the outer surface of the at least one wall of the pair of opposing walls in a direction that is perpendicular to a planar surface of the RFID tag.

37. A container comprising:
   a container body including at least a base and a plurality of walls; and
   a slot in the container body, the slot at least partially defined by a pair of opposing walls with at least one retention projection extending outwardly of an outer surface of at least one wall of the pair of opposing walls, wherein an outwardly facing surface of the at least one retention projection tapers relative to the outer surface of the at least one wall of the pair of opposing walls.

* * * * *